US008278350B2

(12) United States Patent
Kato et al.

(10) Patent No.: US 8,278,350 B2
(45) Date of Patent: Oct. 2, 2012

(54) AGENT FOR SKIN EXTERNAL USE CONTAINING SALT OF ASCORBIC ACID DERIVATIVE, METHOD FOR STABILIZING THE AGENT FOR SKIN EXTERNAL USE, AND STABILIZER

(75) Inventors: Eiko Kato, Chiba (JP); Tadashi Yoneda, Chiba (JP); Eiji Ogata, Chiba (JP)

(73) Assignee: Showa Denko K.K., Tokyo (JP)

( * ) Notice: Subject to any disclaimer, the term of this patent is extended or adjusted under 35 U.S.C. 154(b) by 1289 days.

(21) Appl. No.: 10/575,624

(22) PCT Filed: Oct. 13, 2004

(86) PCT No.: PCT/JP2004/015457
§ 371 (c)(1),
(2), (4) Date: Apr. 13, 2006

(87) PCT Pub. No.: WO2005/034903
PCT Pub. Date: Apr. 21, 2005

(65) Prior Publication Data
US 2007/0140998 A1 Jun. 21, 2007

Related U.S. Application Data

(60) Provisional application No. 60/512,857, filed on Oct. 22, 2003, provisional application No. 60/567,527, filed on May 4, 2004.

(30) Foreign Application Priority Data

Oct. 14, 2003 (JP) .................................. 2003-353669
Apr. 26, 2004 (JP) .................................. 2004-130206

(51) Int. Cl.
*A61K 31/375* (2006.01)
*C07D 307/62* (2006.01)

(52) U.S. Cl. ....................................... 514/474; 549/315

(58) Field of Classification Search .................... 514/99, 514/474; 549/315
See application file for complete search history.

(56) References Cited

U.S. PATENT DOCUMENTS

| 6,124,274 | A | * | 9/2000 | Schehlmann et al. | 514/99 |
| 6,306,915 | B1 | * | 10/2001 | Murata | 516/67 |
| 2005/0222276 | A1 | * | 10/2005 | Schmaus et al. | 514/738 |

FOREIGN PATENT DOCUMENTS

| EP | 1077066 A1 | 2/2001 |
| JP | 8-113525 A | 5/1996 |
| JP | 2002-3330 A | 1/2002 |
| JP | 2002-348228 A | 12/2002 |
| JP | 2003-176217 A | 6/2003 |
| JP | 2003-267856 A | 9/2003 |
| WO | WO 03/069994 * | 8/2003 |
| WO | WO 03/086384 A1 | 10/2003 |

OTHER PUBLICATIONS

T. Motoi, "Skin cosmetics containing ascorbic acid derivatives", 6001 Chemical Abstracts, American Chemical Society, Columbus, Ohio, U.S., vol. 105, No. 24, Dec. 15, 1986, XP002073274, ISSN: 0009-2258.
Patent Abstracts of Japan, vol. 2003, No. 10, Oct. 8, 2003 & JP 2003-176217 A (Showa Denko K.K.). Jun. 24, 2003.
Shigeru Sekine et al., Cosmetics Handbook, Nov. 1, 1996, p. 84.

* cited by examiner

*Primary Examiner* — Fereydoun G Sajjadi
*Assistant Examiner* — Danielle Sullivan
(74) *Attorney, Agent, or Firm* — Sughrue Mion, PLLC

(57) ABSTRACT

An agent for skin external use of the invention contains a salt of higher fatty acid ester of ascorbic acid-2-phosphoric acid ester and a polyhydric alcohol. According to the present invention, occurrence of turbidity or precipitation with time can be prevented to enhance stability even when the agent for skin external use is prepared using a specific salt of higher fatty acid ester of ascorbic acid-2-phosphoric acid ester. Therefore, the present invention is useful for all agents for skin external use, particularly cosmetics.

10 Claims, No Drawings

AGENT FOR SKIN EXTERNAL USE CONTAINING SALT OF ASCORBIC ACID DERIVATIVE, METHOD FOR STABILIZING THE AGENT FOR SKIN EXTERNAL USE, AND STABILIZER

REFERENCE TO RELATED APPLICATIONS

This application is an application filed under 35 U.S.C. §111 (a) claiming benefit pursuant to 35 U.S.C. §119(e) of the filing dates of Provisional Application No. 60/512,857 filed on Oct. 22, 2003 and 60/567,527 filed on May 4, 2004 pursuant to 35 U.S.C. §111(b).

FIELD OF THE INVENTION

The present invention relates to an agent for skin external use and a cosmetic each of which contains a salt of an ascorbic acid derivative and has excellent stability, said ascorbic acid derivative being represented by the following formula (1):

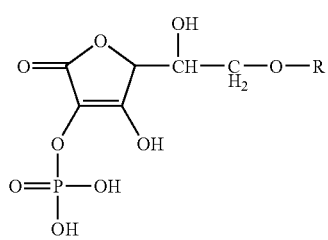

Formula (1)

wherein R is a higher fatty acid residual group.

The present invention also relates to a method for stabilizing the agent for skin external use containing a salt of an ascorbic acid derivative, and a stabilizer.

BACKGROUND OF THE INVENTION

Ascorbic acid and its various derivatives are known as compounds exhibiting efficacy and effects in whitening action, anti-oxidant action, collagen synthesis promotion action, etc., and they are contained in medicines, cosmetics, feeds and the like.

Of the ascorbic acid derivatives, compounds wherein a hydroxyl group at the 2-position is esterified with phosphoric acid and a hydroxyl group at the 6-position is esterified with a higher fatty acid and their salts are hardly oxidized and are stable and amphipathic. Therefore, these compounds have good affinity for living organisms and rapidly penetrate into the organism tissues such as the skin, so that application to medicines, cosmetics, feeds, etc. is expected.

However, when agents for skin external use are prepared using the salts of higher fatty acid esters of ascorbic acid-2-phosphoric acid ester, decomposition of these compounds takes place in the resulting agents, and besides, turbidity or precipitation occurs with time, resulting in a problem of markedly impaired appearance.

In connection with the above, there has been disclosed a whitening agent for skin external use, which is improved in the stability by allowing cyclodextrin to include ascorbic acid or a higher fatty acid ester of ascorbic acid and which uses a polyhydric alcohol as a solvent (Japanese Patent Laid-open Publication No. 113525/1996). In Japanese Patent Laid-open Publication No. 113525/1996, however, there is no description about an agent for skin external use which uses a higher fatty acid ester of ascorbic acid-2-phosphoric acid ester or its salt.

In Japanese Patent Laid-open Publication No. 348228/2002, there is disclosed a composition for skin external use in which ascorbic acid, its ester derivatives, its ether derivatives or their salts are kept in a stable state in aqueous media composed of water and glycol ethers. In this document, however, there is no description about an agent for skin external use which uses a salt of higher fatty acid ester of ascorbic acid-2-phosphoric acid ester.

In Japanese Patent Laid-open Publication No. 3330/2002, there is disclosed a cosmetic which comprises a water-soluble ascorbic acid derivative, such as ascorbic acid phosphoric acid ester magnesium salt, water and 1,2-alkanediol and is stable in spite of passage of time. In this document, however, there is no description about an agent for skin external use which uses a salt of higher fatty acid ester of ascorbic acid-2-phosphoric acid ester.

Further, the present inventors have already proposed an agent for skin external use and a cosmetic in Japanese Patent Laid-open Publication No. 176217/2003. This agent for skin external use contains a salt of higher fatty acid ester of ascorbic acid-2-phosphoric acid ester and has been adjusted to pH 7 to 9 to inhibit decomposition of the salt in the agent and thereby improve stability and solubility.

In the working example in this patent document, a lotion obtained by adding 10% by mass of propylene glycol to an agent for skin external use containing a salt of higher fatty acid ester of ascorbic acid-2-phosphoric acid ester is disclosed, and it is described that decomposition of the salt of higher fatty acid ester of ascorbic acid-2-phosphoric acid ester is inhibited. In this lotion, however, occurrence of turbidity could not be inhibited though decomposition of the salt of higher fatty acid ester of ascorbic acid-2-phosphoric acid ester could be inhibited. Accordingly, from the viewpoint of practical use of an agent for skin external use containing a salt of higher fatty acid ester of ascorbic acid-2-phosphoric acid ester, development of an agent for skin external use which is more effectively prevented from occurrence of turbidity or precipitation with time is still eagerly desired.

DISCLOSURE OF THE INVENTION

It is an object of the present invention to provide an agent for skin external use and a cosmetic each of which is enhanced in the stability (regarding to occurrence of turbidity or precipitation with time), containing a salt of higher fatty acid ester of ascorbic acid-2-phosphoric acid ester, said higher fatty acid ester of ascorbic acid-2-phosphoric acid ester being one of ascorbic acid derivatives and represented by the following formula (1):

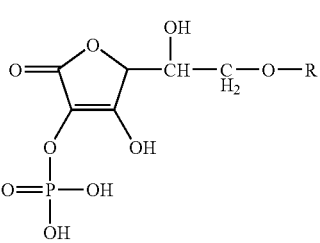

Formula (1)

wherein R is a higher fatty acid residual group.

It is also an object of the present invention to provide, through provision of such an agent for skin external use as mentioned above, a method for stabilizing the agent for skin external use containing a salt of higher fatty acid ester of ascorbic acid-2-phosphoric acid ester and a stabilizer for the agent for skin external use.

Under such circumstances as described above, the present inventors have earnestly studied, and as a result, they have found that an agent for skin external use which is effectively prevented from occurrence of turbidity or precipitation with time can be provided by allowing a salt of higher fatty acid ester of ascorbic acid-2-phosphoric acid ester and a polyhydric alcohol to be present together, preferably by allowing the salt and a specific amount of a specific polyhydric alcohol to be present together. Based on the finding, the present invention has been accomplished.

That is to say, the present invention relates to the following matters.

(1) An agent for skin external use, comprising:
a salt of higher fatty acid ester of ascorbic acid-2-phosphoric acid ester, said higher fatty acid ester of ascorbic acid-2-phosphoric acid ester being represented by the following formula (1):

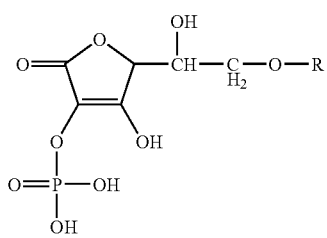

Formula (1)

wherein R is a higher fatty acid residual group, and
a polyhydric alcohol.

(2) The agent for skin external use as stated in (1), wherein R in the formula (1) is a residual group of an aliphatic carboxylic acid of 10 to 20 carbon atoms.

(3) The agent for skin external use as stated in (1) or (2), wherein R in the formula (1) is a residual group of lauric acid, myristic acid, palmitic acid, stearic acid, 2-hexyldecanoic acid or isostearic acid.

(4) The agent for skin external use as stated in any one of (1) to (3), wherein R in the formula (1) is a residual group of palmitic acid.

(5) The agent for skin external use as stated in any one of (1) to (3), wherein R in the formula (1) is a residual group of 2-hexyldecanoic acid.

(6) The agent for skin external use as stated in any one of (1) to (5), wherein the salt of higher fatty acid ester of ascorbic acid-2-phosphoric acid ester is a Na salt, a K salt, a Mg salt or a Zn salt.

(7) The agent for skin external use as stated in any one of (1) to (6), wherein the salt of higher fatty acid ester of ascorbic acid-2-phosphoric acid ester is contained in an amount of 0.01 to 20% by mass.

(8) The agent for skin external use as stated in any one of (1) to (7), wherein the polyhydric alcohol is a dihydric alcohol of 5 or 6 carbon atoms (when the number of carbon atoms is 5 or 6, a hetero atom may be inserted in the carbon chain).

(9) The agent for skin external use as stated in (8), wherein the dihydric alcohol of 5 or 6 carbon atoms is at least one dihydric alcohol selected from the group consisting of triethylene glycol, dipropylene glycol, 3-methyl-1,3-butanediol, 1,2-pentanediol, 1,4-pentanediol, 1,5-pentanediol, 2,4-pentanediol, 2-methyl-2,4-pentanediol, 3-methyl-1,5-pentanediol, 1,2-hexanediol and 1,6-hexanediol.

(10) The agent for skin external use as stated in (8) or (9), wherein the dihydric alcohol of 5 or 6 carbon atoms is contained in an amount of not less than 0.05% by mass and less than 12% by mass.

(11) The agent for skin external use as stated in any one of (1) to (7), wherein the polyhydric alcohol is at least one alcohol selected from the group consisting of dihydric or higher alcohols of 2, 3, 4 or 7 or more carbon atoms (when the number of carbon atoms is 3, 4 or 7 or more, a hetero atom may be inserted in the carbon chain), and the polyhydric alcohol is contained in an amount of 12 to 90% by mass.

(12) The agent for skin external use as stated in (11), wherein the polyhydric alcohol which is a dihydric or higher alcohol of 2, 3, 4 or 7 or more carbon atoms (when the number of carbon atoms is 3, 4 or 7 or more, a hetero atom may be inserted in the carbon chain) is at least one alcohol selected from the group consisting of ethylene glycol, propylene glycol, glycerin, 1,3-butanediol, diethylene glycol, polyethylene glycol, polypropylene glycol and polyglycerin.

(13) The agent for skin external use as stated in any one of (1) to (12), wherein water is further contained.

(14) A cosmetic comprising the agent for skin external use of any one of (1) to (13).

(15) A method for stabilizing an agent for skin external use containing a salt of higher fatty acid ester of ascorbic acid-2-phosphoric acid ester, said higher fatty acid ester of ascorbic acid-2-phosphoric acid ester being represented by the following formula (1):

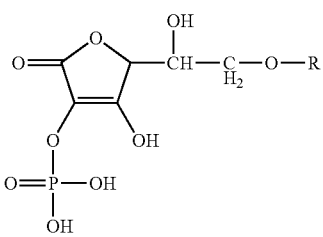

Formula (1)

wherein R is a higher fatty acid residual group,
said method using a polyhydric alcohol.

(16) The method for stabilizing an agent for skin external use as stated in (15), wherein the polyhydric alcohol is a dihydric alcohol of 5 or 6 carbon atoms (when the number of carbon atoms is 5 or 6, a hetero atom may be inserted in the carbon chain).

(17) A stabilizer for an agent for skin external use containing a salt of higher fatty acid ester of ascorbic acid-2-phosphoric acid ester, said higher fatty acid ester of ascorbic acid-2-phosphoric acid ester being represented by the following formula (1):

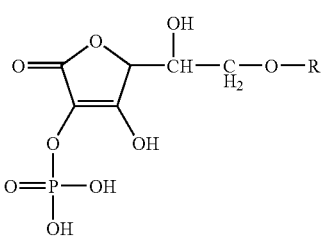

Formula (1)

wherein R is a higher fatty acid residual group,
said stabilizer comprising a polyhydric alcohol.

(18) The stabilizer for an agent for skin external use as stated in (17), wherein the polyhydric alcohol is a dihydric alcohol of 5 or 6 carbon atoms (when the number of carbon atoms is 5 or 6, a hetero atom may be inserted in the carbon chain).

PREFERRED EMBODIMENTS OF THE INVENTION

The present invention is described in detail hereinafter.

(A) Salt of Higher Fatty Acid Ester of Ascorbic Acid-2-phosphoric Acid Ester

First, the salt of higher fatty acid ester of ascorbic acid-2-phosphoric acid ester for use in the invention is described.

The higher fatty acid ester of ascorbic acid-2-phosphoric acid ester which becomes a main structure of the salt is a compound represented by the formula (1). In the formula (1), R is a higher fatty acid residual group, namely an acyl group derived from a higher fatty acid, and the higher fatty acid is, for example, an aliphatic carboxylic acid of 10 to 20 carbon atoms. Preferred examples of the aliphatic carboxylic acids include lauric acid, myristic acid, palmitic acid, stearic acid, 2-hexyldecanoic acid and isostearic acid. Of these, palmitic acid and 2-hexyldecanoic acid are more preferable.

The salt of higher fatty acid ester of ascorbic acid-2-phosphoric acid ester for use in the invention is preferably a compound wherein a phosphoric acid residual group to constitute a phosphoric acid ester linkage at the 2-position in the higher fatty acid ester of ascorbic acid-2-phosphoric acid ester, said higher fatty acid ester of ascorbic acid-2-phosphoric acid ester being a compound wherein phosphoric acid is ester linked to a hydroxyl group at the 2-position of ascorbic acid and a higher fatty acid is ester linked to a hydroxyl group at the 6-position thereof, and a base form a salt.

Preferred examples of the salts of higher fatty acid ester of ascorbic acid-2-phosphoric acid ester include Na salts, K salts, Ca salts, Mg salts, and Zn salts. Of these, Na salts are more preferable. In the present invention, the salts of higher fatty acid ester of ascorbic acid-2-phosphoric acid ester may be used singly or in combination of two or more kinds.

In the present invention, the salt of higher fatty acid ester of ascorbic acid-2-phosphoric acid ester is added so that the salt is contained in an amount of usually 0.01 to 20% by mass, preferably 0.05 to 12% by mass, more preferably 0.2 to 10% by mass, in the whole amount of the agent for skin external use. When the salt of higher fatty acid ester of ascorbic acid-2-phosphoric acid ester is contained in this amount in the agent for skin external use, the agent rapidly penetrates into the skin and can exhibit efficacy and effects required for agents for skin external use, so that such an amount is preferable.

(B) Polyhydric Alcohol

In the present description, the polyhydric alcohol means a compound which is selected from alcohols having two or more hydroxyl groups in a molecule. And the polyhydric alcohol includes dihydric alcohols, trihydric alcohols, ethers of trihydric alcohols, sugar alcohols, monosaccharides and oligosaccharides (2-10 saccharides).

Examples of the polyhydric alcohols include dihydric alcohols, such as ethylene glycol, propylene glycol, 1,3-butanediol, 3-methyl-1,3-butanediol, 1,2-pentanediol, 1,4-pentanediol, 1,5-pentanediol, 2,4-pentanediol, 2-methyl-2,4-pentanediol, 3-methyl-1,5-pentanediol, 1,2-hexanediol, 1,6-hexanediol, diethylene glycol, triethylene glycol, polyethylene glycol, dipropylene glycol, polypropylene and glycol; trihydric alcohols, such as glycerin; ethers of trihydric alcohols, such as diglycerin and polyglycerin; sugar alcohols, such as mannitol, sorbitol, xylitol, maltitol, erythritol and pentaerythritol; monosaccharides, such as glucose, fructose and xylose; and oligosaccharides, such as sucrose, lactose, maltose and trehalose.

Of these, one preferred example is a dihydric alcohol having 5 or 6 carbon atoms. The carbon chain to constitute the alcohol may be branched, and if the number of carbon atoms is 5 or 6, a hetero atom may be inserted in the carbon chain. That is to say, the alcohol has only to have 5 or 6 carbon atoms in all, and the carbon chain constituted of these carbon atoms may be an intermittent carbon chain having a hetero atom between the carbon atoms.

That is to say, a hetero atom may be inserted midway on the carbon chain that constitutes the alcohol, and the hetero atom is, for example, oxygen, nitrogen or sulfur.

Examples of the dihydric alcohols of 5 or 6 carbon atoms include triethylene glycol, dipropylene glycol, 3-methyl-1,3-butanediol, 1,2-pentanediol, 1,4-pentanediol, 1,5-pentanediol, 2,4-pentanediol, 2-methyl-2,4-pentanediol, 3-methyl-1,5-pentanediol, 1,2-hexanediol and 1,6-hexanediol.

Of these, preferable are 1,2-pentanediol, 1,4-pentanediol, 1,5-pentanediol, 2,4-pentanediol, 1,2-hexanediol and 1,6-hexanediol, and more preferable are 1,2-pentanediol and 1,2-hexanediol.

These dihydric alcohols of 5 or 6 carbon atoms may be used singly or in combination of two or more kinds.

In the agent for skin external use of the invention, the dihydric alcohol of 5 or 6 carbon atoms has only to be contained in an amount suitable for inhibiting occurrence of turbidity or precipitation of the resulting agent for skin external use, and specifically, the dihydric alcohol of 5 or 6 carbon atoms is desirably contained in an amount of usually not less than 0.05% by mass and less than 12% by mass, preferably 0.5 to 11% by mass, more preferably 0.5 to 10% by mass, in the whole amount of the agent for skin external use.

By virtue of use of the specific dihydric alcohol, the amount of the alcohol can be held down to that of the above range, and therefore, a feeling in the use of the agent for skin external use is better than that in the case where other polyhydric alcohols are used.

Another preferred example is a polyhydric alcohol which is a dihydric or higher alcohol of 2, 3, 4 or 7 or more carbon atoms. The carbon chain to constitute the polyhydric alcohol may be branched, and if the number of carbon atoms is 3, 4 or 7 or more, a hetero atom may be inserted in the carbon chain. That is to say, the polyhydric alcohol has only to have 2, 3, 4 or 7 or more carbon atoms in all, and if the number of carbon atoms is 3, 4 or 7 or more, the carbon chain constituted of these carbon atoms may be an intermittent carbon chain having a hetero atom between the carbon atoms.

That is to say, a hetero atom may be inserted midway on the carbon chain that constitutes the polyhydric alcohol, and the hetero atom is, for example, oxygen, nitrogen or sulfur.

Examples of the polyhydric alcohols which are dihydric or higher alcohols of 2, 3, 4 or 7 or more carbon atoms include ethylene glycol, propylene glycol, glycerin, 1,3-butanediol, diethylene glycol, polyethylene glycol, polypropylene glycol and polyglycerin.

Of these, preferable are propylene glycol, glycerin, 1,3-butanediol, diethylene glycol, polyethylene glycol and polyglycerin, and more preferable are propylene glycol and 1,3-butanediol.

These polyhydric alcohols which are dihydric or higher alcohols of 2, 3, 4 or 7 or more carbon atoms, may be used singly or in combination of two or more kinds.

The polyhydric alcohol which is a dihydric or higher alcohol of 2, 3, 4 or 7 or more carbon atoms has only to be added in an amount suitable for inhibiting occurrence of turbidity or precipitation of the resulting agent for skin external use, but specifically, the polyhydric alcohol needs to be contained in an amount of 12 to 90% by mass, preferably 15 to 90% by mass, more preferably 20 to 90% by mass, in the whole amount of the agent for skin external use. When the polyhydric alcohol which is a dihydric or higher alcohol of 2, 3, 4 or 7 or more carbon atoms is contained in an amount of 12 to 90% by mass, occurrence of turbidity or precipitation of the resulting agent for skin external use with time can be effectively inhibited. If the amount of the polyhydric alcohol is less than 12% by mass, occurrence of turbidity or precipitation cannot be sufficiently inhibited in some cases, and if the amount thereof exceeds 90% by mass, occurrence of turbidity or precipitation cannot be sufficiently inhibited in some cases either, so that such amounts are undesirable.

The concentration of the polyhydric alcohol in the agent for skin external use can be measured by a general method such as quantitative determination using gas chromatography.

(C) Other Components

To the agent for skin external use of the invention, components generally used for agents for skin external use can be added in addition to the salt of higher fatty acid ester of ascorbic acid-2-phosphoric acid ester and the polyhydric alcohol.

Examples of such an ingredient include hydrocarbons such as ozokerite, α-olefin oligomer, light isoparaffin, light liquid isoparaffin, squalene, squalane, synthetic squalane, phytosqualane, ceresin, paraffin, polyethylene powder, polybutene, microcrystalline wax, liquid isoparaffin, liquid paraffin, mineral oil and vaseline;

natural waxes such as jojoba oil, carnauba wax, candelilla wax, rice bran wax, shellac, lanolin, mink sebaceous wax, spermaceti wax, sugarcane wax, sperm whale oil, beeswax and montan wax, natural fats and fatty oils such as avocado oil, almond oil, olive oil, extra virgin olive oil, sesame seed oil, rice bran oil, rice oil, rice germ oil, corn oil, safflower oil, soybean oil, maize oil, rape seed oil, persic oil, palm kernel oil, palm oil, castor oil, sunflower oil, high oleic sunflower oil, grape seed oil, cotton seed oil, coconut oil, hydrogenated coconut oil, beef tallow, hydrogenated oil, horse oil, mink oil, yolk oil, yolk fat oil, rose hip oil, kukui nut oil, evening primrose oil, wheat germ oil, peanut oil, *Camellia jeponica* oil, *Camellia kissi* oil, cacao butter, Japan wax, beef bone tallow, nest's-foot oil, swine tallow, equine tallow, ovine tallow, shea butter, *macadamia* nut oil and meadowfoam seed oil;

fatty acids such as lauric acid, myristic acid, palmitic acid, stearic acid, behenic acid, oleic acid, linoleic acid, linolenic acid, γ-linolenic acid, isostearic acid, 12-hydroxystearic acid, undecylenic acid and coconut oil fatty acid;

higher monohydric alcohols such as isostearyl alcohol, octyl dodecanol, hexyl decanol, cholesterol, phytosterol, lauryl alcohol, myristyl alcohol, cetyl alcohol, stearyl alcohol, oleyl alcohol, behenyl alcohol and cetostearyl alcohol;

alkylglyceryl ethers such as batyl alcohol, chimyl alcohol, serachyl alcohol and isostearyl glyceryl ether;

esters such as isopropyl myristate, butyl myristate, isopropyl palmitate, ethyl stearate, butyl stearate, ethyl oleate, ethyl linoleate, isopropyl linoleate, cetyl caprylate, hexyl laurate, isooctyl myristate, decyl myristate, myristyl myristate, cetyl myristate, octadecyl myristate, cetyl palmitate, stearyl stearate, decyl oleate, oleyl oleate, cetyl ricinoleate, isostearyl laurate, isotridecyl myristate, isocetyl myristate, isostearyl myristate, octyldodecyl myristate, 2-ethylhexyl palmitate, isocetyl palmitate, isostearyl palmitate, 2-ethylhexyl stearate, isocetyl stearate, isodecyl oleate, octyldodecyl oleate, octyldodecyl ricinoleate, ethyl isostearate, isopropyl isostearate, cetyl 2-ethylhexanoate, cetostearyl 2-ethylhexanoate, stearyl 2-ethylhexanoate, hexyl isostearate, ethylene glycol dioctanoate, ethylene glycol dioleate, propylene glycol dicaprylate, propylene glycol dicaprylate/dicaprate, propylene glycol dicaprate, propylene glycol dioleate, neopentyl glycol dicaprate, neopentyl glycol dioctanoate, glyceryl tricaprylate, glyceryl tri 2-ethyl hexanoate, glyceryl tricaprylate/tricaprate, glyceryl tricaprylate/tricaprate/tristearate, glyceryl triundecylate, glyceryl triisopalmitate, glyceryl triisostearate, trimethylolpropane tri 2-ethylhexanoate, trimethylolpropane triisostearate, pentaerythrityl tetra 2-ethylhexanoate, pentaerythrityl tetramyristate, pentaerythrityl tetraisostearate, diglyceryl tetraisostearate, octyldodecyl neopentanotae, isocetyl octanoate, isostearyl octanoate, 2-ethylhexyl isopelargonate, hexyldecyl dimethyloctanoate, octyldodecyl dimethyloctanoate, 2-ethylhexyl isopalmitate, isocetyl isostearate, isostearyl isostearate, octyldodecyl isostearate, lauryl lactate, myristyl lactate, cetyl lactate, octyldodecyl lactate, triethyl citrate, acetyltriethyl citrate, acetyltributyl citrate, trioctyl citrate, triisocetyl citrate, trioctyldodecyl citrate, diisostearyl malate, 2-ethylhexyl hydroxystearate, di 2-ethylhexyl succinate, diisopropyl adipate, diisobutyl adipate, dioctyl adipate, diheptylundecyl adipate, sebacate diethyl, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoyl hydroxystearate, stearyl 12-stearoyl hydroxystearate, isostearyl 12-stearoyl hydroxystearate, polyoxyethylene (3) polyoxypropylene (1) cetyl ether acetate, polyoxyethylene (3) polyoxypropylene (1) isocetyl ether acetate, isononyl isononanoate, octyl isononanoate, tridecyl isononanoate and isotridecyl isononanoate;

silicone oils such as methyl polysiloxane, methylphenyl polysiloxane, methyl hydrogen polysiloxane, methyl cyclopolysiloxane, octamethyl cyclotetrasiloxane, decamethyl cyclopentasiloxane, dodecamethyl cyclohexasiloxane, octamethyl trisiloxane, decamethyl tetrasiloxane, tetradecamethyl hexasiloxane, highly polymerized methyl polysiloxane, dimethylsiloxane-methyl(polyoxyethylene)siloxane-methyl(pol yoxypropylene)siloxane copolymer, dimethylsiloxane-methyl(polyoxyethylene)siloxane copolymer, dimethylsiloxane-methyl(polyoxypropylene)siloxane copolymer, dimethylsiloxane-methylcetyl oxysiloxane copolymer, dimethylsiloxane-methyl stearoxysiloxane copolymer, polyether modified silicone, alcohol modified silicone, alkyl modified silicone and amino modified silicone;

polymers such as sodium alginate, carrageenan, agar, furcellaran, guar gum, quince seed, *Amorphophalus konjak* (arum root) mannan, tamarind gum, tara gum, dextrin, starch, locust bean gum, gum arabic, gum ghatti, karaya gum, gum tragacanth, arabinogalactan, pectin, quince, chitosan, curdlan, xanthan gum, gellan gum, cyclodextrin, dextran, pullulan, microcrystalline cellulose, methyl cellulose, ethyl cellulose, hydroxyethyl cellulose, hydroxypropyl cellulose, hydroxypropylmethyl cellulose, carboxymethyl cellulose, carboxy starch, cationized cellulose, starch phosphate ester, cationized guar gum, carboxymethyl-hydroxypropylated guar gum, hydroxypropylated guar gum, albumin, casein, gelatin, sodium polyacrylate, polyacrylic amide, carboxyvinyl polymer, polyethylene imine, highly polymerized polyethylene glycol, polyvinyl alcohol, polyvinyl pyrrolidone, polyvinyl ether, polyacryl amide, acrylic acid polymer, methacrylic acid polymer, maleic acid polymer, vinylpyridine polymer, ethylene/acrylic acid copolymer, vinyl pyrrolidone based polymer, vinyl alcohol/vinyl pyrrolidone copolymer, nitrogen-substituted acrylamide based polymer, amino modified silicone, cationized polymer, dimethylacryl ammonium based polymer, acrylic acid based anion polymer, methacrylic acid based anion polymer, modified silicone, acrylate/methacrylate alkyl (C 10 to 30) copolymer and polyoxyethylene/polyoxypropylene copolymer;

monohydric alcohols such as ethanol, isopropyl alcohol, 1-butanol, 2-butanol and benzyl alcohol;

anionic surfactants such as coconut oil fatty acid potassium, coconut oil fatty acid sodium, coconut oil fatty acid triethanolamine, potassium laurate, sodium laurate, triethanolamine laurate, potassium myristate, sodium myristate, isopropanolamine myristate, potassium palmitate, sodium palmitate, isopropanolamine palmitate, potassium stearate, sodium stearate, triethanolamine stearate, potassium oleate, sodium oleate, castor oil fatty acid sodium, zinc undecylate, zinc laurate, zinc myristate, magnesium myristate, zinc palmitate, zinc stearate, calcium stearate, magnesium stearate, aluminum stearate, calcium myristate, magnesium myristate, aluminum dimyristate, aluminum isostearate, polyoxyethylene lauryl ether acetate, sodium polyoxyethylene lauryl ether acetate, polyoxyethylene tridecyl ether acetate, sodium polyoxyethylene tridecyl ether acetate, sodium stearoyl lactate, sodium isostearoyl lactate, sodium lauroyl sarcosine, coconut oil fatty acid sarcosine, sodium coconut oil fatty acid sarcosine, coconut oil fatty acid sarcosine triethanolamine, lauroyl sarcosine, potassium lauroyl sarcosine, lauroyl sarcosine triethanolamine, oleoyl sarcosine, sodium myristoyl sarcosine, sodium stearoyl glutamate, coconut oil fatty acid acyl glutamic acid, potassium coconut oil fatty acid acyl glutamate, sodium coconut oil fatty acid acyl glutamate, coconut oil fatty acid acyl glutamate triethanolamine, lauroylacyl glutamic acid, potassium lauroylacyl glutamate, sodium lauroylacyl glutamate, lauroylacyl glutamate triethanolamine, myristoylacyl glutamic acid, potassium myristoylacyl glutamate, sodium myristoylacyl glutamate, stearoylacyl glutamic acid, potassium stearoylacyl glutamate, disodium stearoylacyl glutamate, sodium hydrogenated beef tallow fatty acid acyl glutamate, sodium coconut oil fatty acid/hydrogenated beef tallow fatty acid acyl glutamate, sodium coconut oil fatty acid methylalanine, lauroyl methylalanine, sodium lauroyl methylalanine, lauroyl methylalanine triethanolamine, sodium myristoyl methylalanine, sodium lauroyl methyltaurine, potassium coconut oil fatty acid methyltaurine, sodium coconut oil fatty acid methyltaurine, magnesium coconut oil fatty acid methyltaurine, sodium myristoyl methyltaurine, sodium palmitoyl methyltaurine, sodium stearoyl methyltaurine, sodium oleoyl methyltaurine, sodium alkane sulfonate, sodium tetradecene sulfonate, sodium sulfosuccinate dioctyl, disodium lauryl sulfosuccinate, sodium coconut oil fatty acid ethyl ester sulfonate, sodium lauryl sulfate, triethanolamine lauryl sulfate, sodium cetyl sulfate, triethanolamine alkyl (11, 13,15) sulfate, sodium alkyl (12,13) sulfate, triethanolamine alkyl (12,13) sulfate, alkyl (12,14,16) ammonium sulfate, diethanolamine alkyl (12 to 13) sulfate, triethanolamine alkyl (12 to 14) sulfate, triethanolamine alkyl (12 to 15) sulfate, magnesium coconut oil alkyl sulfate/triethanolamine, lauryl ammonium sulfate, potassium lauryl sulfate, magnesium lauryl sulfate, monoethanolamine lauryl sulfate, diethanolamine lauryl sulfate, sodium myristyl sulfate, sodium stearylsulfate, sodium oleyl sulfate, triethanolamine oleyl sulfate, sodium polyoxyethylene lauryl ether sulfate, triethanolamine polyoxyethylene lauryl ether sulfate, sodium polyoxyethylene (1) alkyl (11,13,15) ether sulfate, triethanolamine polyoxyethylene (1) alkyl (11,13,15) ether sulfate, sodium polyoxyethylene (3) alkyl (11 to 15) ether sulfate, sodium polyoxyethylene (2) alkyl (12,13) ether sulfate, sodium polyoxyethylene (3) alkyl (12 to 14) ether sulfate, sodium polyoxyethylene (3) alkyl (12 to 15) ether sulfate, sodium polyoxyethylene (2) lauryl ether sulfate, sodium polyoxyethylene (3) myristyl ether sulfate, sodium higher fatty acid alkanol amide sulfate ester, lauryl phosphate, sodium lauryl phosphate, potassium cetyl phosphate, diethanolamine cetyl phosphate, polyoxyethylene oleyl ether phosphate, polyoxyethylene lauryl ether phosphate, sodium polyoxyethylene lauryl ether phosphate, polyoxyethylene cetyl ether phosphate, sodium polyoxyethylene cetyl ether phosphate, polyoxyethylene stearyl ether phosphate, sodium polyoxyethylene oleyl ether phosphate, polyoxyethylene alkylphenyl ether phosphate, sodium polyoxyethylene alkylphenyl ether phosphate, triethanolamine polyoxyethylene alkylphenyl ether phosphate, polyoxyethylene octyl ether phosphate, polyoxyethylene (10) alkyl (12,13) ether phosphate, polyoxyethylene alkyl (12 to 15) ether phosphate, polyoxyethylene alkyl (12 to 16) ether phosphate, triethanolamine polyoxyethylene lauryl ether phosphate and diethanolamine polyoxyethylene oleyl ether phosphate;

cationic surfactants such as dioctylamine, dimethylstearylamine, trilaurylamine, diethylaminoethylamide stearate, lauryl trimethylammonium chloride, cetyl trimethylammonium chloride, cetyl trimethylammonium bromide, cetyl trimethylammonium saccharin, stearyl trimethylammonium chloride, alkyl (20 to 22) trimethylammonium chloride, lauryl trimethylammonium bromide, alkyl (16,18) trimethylammonium chloride, stearyl trimethylammonium bromide, stearyl trimethylammonium saccharin, alkyl (28) trimethylammonium chloride, di(polyoxyethylene) oleyl methylammonium (2EO) chloride, dipolyoxyethylene stearyl methylammonium chloride, polyoxyethylene (1) polyoxypropylene (25) diethylmethylammonium chloride, tri(polyoxyethylene) stearyl ammonium (5EO) chloride, distearyl dimethylammonium chloride, dialkyl (12 to 15) dimethylammonium chloride, dialkyl (12 to 18) dimethylammonium chloride, dialkyl (14 to 18) dimethylammonium chloride, dicocoyl dimethylammonium chloride, dicetyl dimethylammonium chloride, isostearyllauryl dimethylammonium chloride, benzalkonium chloride, myristyl dimethylbenzyl ammonium chloride, lauryl dimethyl(ethylbenzyl) ammonium chloride, stearyl dimethylbenzyl ammonium chloride, lauryl pyridinium chloride, cetyl pyridinium chloride, lauroyl cholamino formylmethyl pyridinium chloride, stearoyl cholamino formylmethyl pyridinium chloride, alkyl isoquinolinium bromide, methyl benzethonium chloride and benzethonium chloride;

ampholytic surfactants such as 2-alkyl-N-carboxymethyl-N-hydroxyethyl imidazolium betaine, alkyldiamino ethyl glycine hydrochloride, sodium lauryldiamino ethyl glycine, sodium undecyl hydroxyethyl imidazolium betaine, undecyl-N-carboxymethyl imidazolium betaine, disodium coconut oil fatty acid acyl-N-carboxyethyl-N-hydroxyethyl ethylenediamine, disodium coconut oil fatty acid acyl-N-carboxyethoxyethyl-N-carboxyethyl ethylenediamine, disodium coconut oil fatty acid acyl-N-carboxymethoxyethyl-N-carboxymethyl ethylenediamine, sodium laurylamino propionate, sodium laurylamino dipropionate, triethanolamine laurylamino propionate, sodium palm oil fatty acid acyl-N-carboxymethyl-N-hydroxyethyl ethylenediamine, betaine lauryldimethylamino acetate, betaine coconut oil alkyldimethylamino acetate, betaine stearyl dimethylamino acetate, sodium stearyldimethyl betaine, coconut oil fatty acid amidopropyl betaine, palm oil fatty acid amidopropyl betaine, amidopropyl acetate betaine laurate, amidopropyl betaine ricinoleate, stearyl dihydroxyethyl betaine and lauryl hydroxysulfobetaine;

nonionic surfactants such as polyoxyethylene (10) alkyl (12,13) ether, polyoxyethylene lauryl ether, polyoxyethylene cetyl ether, polyoxyethylene stearyl ether, polyoxyethylene oleyl ether, polyoxyethylene (3,7,12) alkyl (12 to 14) ether, polyoxyethylene tridecyl ether, polyoxyethylene myristyl ether, polyoxyethylene-sec-alkyl (14) ether, polyoxyethylene isocetyl ether, polyoxyethylene cetostearyl ether, polyoxyethylene (2,10,20) isostearyl ether, polyoxyethylene oleylcetyl ether, polyoxyethylene (20) arachyl ether, polyoxyethylene octyldodecyl ether, polyoxyethylene behenyl ether, polyoxyethylene octylphenyl ether, polyoxyethylene nonylphenyl ether, polyoxyethylene dinonylphenyl ether, polyoxyethylene (1) polyoxypropylene (1,2,4,8) cetyl ether, polyoxyethylene (5) polyoxypropylene (1,2,4,8) cetyl ether, polyoxyethylene (10) polyoxypropylene (1,2,4,8) cetyl ether, polyoxyethylene (20) polyoxypropylene (1,2,4,8) cetyl ether, polyoxyethylene polyoxypropylene lauryl ether, polyoxyethylene (3) polyoxypropylene (34) stearyl ether, polyoxyethylene (4) polyoxypropylene (30) stearyl ether, polyoxyethylene (34) polyoxypropylene (23) stearyl ether, polyoxyethylene polyoxypropylene cetyl ether, polyoxyethylene polyoxypropylene decyltetradecyl ether, polyethylene glycol monolaurate, ethylene glycol monostearate, polyethylene glycol monostearate, polyethylene glycol monooleate, ethylene glycol fatty acid ester, self-emulsifying ethylene glycol monostearate, diethylene glycol laurate, polyethylene glycol myristate, polyethylene glycol palmitate, diethylene glycol stearate, self-emulsifying polyethylene glycol (2) monostearate, polyethylene glycol isostearate, ethylene glycol dioctanoate, diethylene glycol dilaurate, polyethylene glycol dilaurate, polyethylene glycol (150) dipalmitate, ethylene glycol distearate, diethylene glycol distearate, polyethylene glycol distearate, ethylene glycol dioleate, polyethylene glycol dioleate, polyethylene glycol diricinoleate, polyoxyethylene (20) sorbitan monolaurate, polyoxyethylene (20) sorbitan monopalmitate, polyoxyethylene (6) sorbitan monostearate, polyoxyethylene (20) sorbitan monostearate, polyoxyethylene (20) sorbitan tristearate, polyoxyethylene (6) sorbitan monooleate, polyoxyethylene (20) sorbitan monooleate, polyoxyethylene (20) sorbitan trioleate, polyoxyethylene (20) coconut oil fatty acid sorbitan, polyoxyethylene (10 to 80) sorbitan monolaurate, polyoxyethylene sorbitan tristearate, polyoxyethylene (20) sorbitan isostearate, polyoxyethylene (150) sorbitan tristearate, polyoxyethylene castor oil, polyoxyethylene hydrogenated castor oil, polyoxyethylene (10) hydrogenated castor oil, polyoxyethylene (20) hydrogenated castor oil, polyoxyethylene (40) hydrogenated castor oil, polyoxyethylene (50) hydrogenated castor oil, polyoxyethylene (60) hydrogenated castor oil, lipophilic glycerin monostearate, lipophilic glycerin monooleate, self-emulsifying glycerin monostearate, coconut oil fatty acid glyceryl, glycerin laurate, glyceryl myristate, glyceryl isostearate, glyceryl ricinoleate, glyceryl monohydroxystearate, glycerin oleate, glyceryl linoleate, glyceryl erucate, glyceryl behenate, wheat germ oil fatty acid glyceride, safflower oil fatty acid glyceryl, hydrogenated soybean fatty acid glyceryl, saturated fatty acid glyceride, cotton seed oil fatty acid glyceryl, monomyristate glyceryl monoisostearate, mono tallowate glyceride, monolanolin fatty acid glyceryl, glyceryl sesquioleate, glyceryl distearate, glyceryl diisostearate, glyceryl diarachidate, sorbitan monolaurate, sorbitan monopalmitate, sorbitan monostearate, sorbitan monoisostearate, sorbitan monooleate, sorbitan sesquistearate, sorbitan sesquioleate, sorbitan tristearate, sorbitan trioleate, coconut oil fatty acid sorbitan, sorbitan isostearate, sorbitan sesquiisostearate, sorbitan distearate, diglyceryl isopalmitate, poly(4 to 10)glyceryl monolaurate, poly(10)glyceryl monomyristate, poly(2 to 10)glyceryl monostearate, poly(2 to 10)glyceryl monoisostearate, poly(2 to 10)glyceryl monooleate, diglyceryl sesquioleate, poly(2 to 10)glyceryl diisostearate, poly(6 to 10)glyceryl distearate, diglyceryl triisostearate, poly(10)glyceryl tristearate, poly(10)glyceryl trioleate, poly(2)glyceryl tetraisostearate, decaglyceryl pentastearate, poly(6 to 10)glyceryl pentaoleate, poly(10)glyceryl heptastearate, decaglyceryl decastearate, poly(10)glyceryl decaoleate, concentrated poly (6)glyceryl ricinoleate, sucrose fatty acid ester, coconut oil fatty acid sucrose ester, alkyl glucoside, coconut oil alkyl dimethylamine oxide, lauryl dimethylamine oxide, dihydroxyethyl lauryl dimethylamine oxide, stearyl dimethylamine oxide, oleyl dimethylamine oxide and polyoxyethylene coconut oil alkyl dimethylamine oxide;

natural surfactants such as saponin, lecithin, soybean phospholipid, hydrogenated soybean phospholipid, soybean lysophospholipid, hydrogenated soybean lysophospholipid, yolk lecithin, hydrogenated yolk lysophosphatidylcholine, phosphatidylcholine, phosphatidylethanolamine, phosphatidylserine, sphingophospholipid, sphingomyelin, ganglioside, bile acid, cholic acid, deoxycholic acid, sodium cholate, sodium deoxycholate, spiculisporic acid, rhamnolipid, trehalose lipid, sophorolipid and mannosyl erythritol lipid;

ultraviolet ray absorbers such as: para-aminobenzoic acid derivatives such as para-aminobenzoic acid, ethyl para-aminobenzoate, glyceryl para-aminobenzoate, amyl para-dimethyl aminobenzoate and 2-ethylhexyl para-dimethyl aminobenzoate; cinnamic acid derivatives such as benzyl cinnamate, mono-2-ethyl hexanoate glyceryl dipara-methoxycinnamate, methyl 2,4-diisopropyl cinnamate, ethyl 2,4-diisopropyl cinnamate, potassium para-methoxycinnamate, sodium para-methoxycinnamate, isopropyl para-methoxycinnamate, 2-ethylhexyl para-methoxycinnamate, 2-ethoxyethyl para-methoxycinnamate and ethyl para-ethoxycinnamate; urocanic acid derivatives such as urocanic acid and ethyl urocanate; benzophenone derivatives such as 2,4-dihydroxybenzophenone, 2,2', 4,4'-tetrahydroxybenzophenone, sodium 2-hydroxy-4-methoxy-5-sulfobenzophenone, 2-hydroxy-4-methoxybenzophenone-5-sulfonate, 2-hydroxy-4-methoxybenzophenone, 2,2'-dihydroxy-4,4'-dimethoxybenzophenone and sodium 2,2'-dihydroxy-4,4'-dimethoxy-5-sulfobenzophenone; salicylic acid derivatives such as ethylene glycol salicylate, salicylate-2-ethylhexyl, phenyl salicylate, benzyl salicylate, p-tert-butylphenyl salicylate, homomenthyl salicylate and salicylate-3,3,5-trimethylcyclohexyl; 2-(2'-hydroxy-5'-methoxyphenyl)benzotriazole and 4-tert-butyl-4'-methoxybenzoyl methane;

powders and color materials such as: kaolin, silicic anhydride, magnesium aluminum silicate, sericite, talc, boron nitride, mica, montmorillonite, hemp cellulose powder, wheat starch, silk powder, maize starch; natural dyes such as nitro dyes, azo dyes, nitroso dyes, triphenylmethane dyes, xanthene dyes, quinoline dyes, anthraquinone dyes, indigo dyes, pyrene dyes, phthalocyanine dyes, flavonoid, quinone, porphyrin, water soluble annatto, sepia powder, caramel, guaiazulene, gardenia blue, gardenia yellow, cochineal, shikonin, sodium copper chlorophyllin, paprika dye, safflower red, safflower yellow, laccaic acid and riboflavin butyrate ester; carbon black, yellow iron oxide, black iron oxide, red iron oxide, iron blue, ultramarine blue, zinc oxide, chromium oxide, titanium oxide, black titanium oxide, zirconium oxide, chromium hydroxide, alumina, magnesium oxide, barium sulfate, aluminum hydroxide, calcium carbonate, lithium cobalt titanate, manganese violet and pearl pigment;

plant extracts such as *Angelica keiskei* extract, *Uncaria gambir* extract, avocado extract, sweet hydrangea leaf extract, *Gynostemma pentaphyllum* makino extract, *Althaea officinalis* extract, *Arnica montana* extract, oil soluble *Arnica montana* extract, almond extract, aloe extract, Japanese styrax benzoin extract, *Ginkgo biloba* extract, Stinging nettle extract, *Orris rhizome* root extract, fennel extract, turmeric extract, dog rose fruit extract, Echinacea leaf extract, *Scutellaria* root extract, *Phellodendron* bark extract, Japanese captis extract, barley extract, okura extract, *Hypericum perforatum* extract, oil soluble *Hypericum perforatum* extract, *Lamium album* extract, oil soluble *Lamium album* extract, *Ononis spinosa* root extract, *Nasturtium officinale* extract, orange extract, orange flower water, seaweed extract, persimmon tannin, *pueraria* root extract, Japanese valerian extract, cattail extract, Chamomile (*matricaria*) extract, oil soluble Chamomile (*matricaria*) extract, Chamomile (matricaria) distillate, *Avena sativa* (oat) kernel extract, carrot extract, oil soluble carrot extract, carrot oil, *Artemisia capillaris* extract, *Glycyrrhiza glabra* (licorice) extract, powdered *Glycyrrhiza glabra* (licorice) extract, *Glycyrrhiza glabra* (licorice) extract flavonoid, cantharides tincture, raspberry extract, kiwi extract, *cinchona* extract, cucumber extract, apricot kernel extract, quince seed extract, *gardenia florida* extract, *Sasa albomarginata* extract, *Sophora* root extract, walnut shell extract, *Citrus paradisi* (grapefruit) extract, *Clematis vitalba* leaf extract, black sugar extract, *chlorella* extract, mulberry bark extract, Cinnamon bark extract, Gentian extract, *Geranium* herb extract, black tea extract, *Nuphar* extract, burdock root extract, oil soluble burdock root extract, wheat germ extract, hydrolyzed wheat powder, rice bran extract, fermented rice bran extract, *Symphytum officinale* (comfrey) extract, *Asiasarum* root extract, *Crocus sativus* (saffron) extract, *Saponaria officinalis* extract, oil soluble salvia extract, *Crataegus cuneata* fruit extract, *Zanthoxylum* fruit extract, *Lentinus edodes* extract, powdered *Lentinus edodes* extract, *Rehmannia* root extract, *Lithospermum* root extract, oil soluble *Lithospermum* root extract, *Perilla* herb extract, linden extract, oil soluble *Tilia europaea* extract, *Filipendula* extract, Peony root extract, *Coix lacryma-jobi* extract, ginger extract, oil soluble ginger extract, ginger tincture, *Acorus calamus* root extract, *Betula pendula* (birch) extract, oil soluble *Betula alba* (birch) extract, *Betula pendula* (birch) sap, *Lonicera japonica* extract, *Equisetum arvense* extract, oil soluble *Equisetum arvense* extract, scordinin, stevia extract, ivy extract, *Crataegus oxyacantha* (whitethorn) extract, *sambucus* extract, *Juniperus communis* extract, *Achillea milefolium* extract, oil soluble *Achillea milefolium* extract, *Mentha piperita* (peppermint) extract, *Salvia officinalis* (sage) extract, oil soluble *Salvia officinalis* (sage) extract, *Salvia officinalis* (sage) water, *Malva Sylvestris* (mallow) extract, *Apium graveolens* (celery) extract, *Cnidium officinale* extract, *Cnidium officinale* water, *Swertia* herb extract, *Glycine max* (soybean) extract, Jujube extract, thyme extract, green tea extract, tea leaf dry distilled solution, tea seed extract, clove extract, *Citrus unshiu* peel extract, *Camellia japonica* extract, *Centella asiatica* extract, oil soluble walnut extract, duku extract, *Terminalia sericea* extract, *Capsicum* tincture, Japanese angelica root extract, oil soluble Japanese angelica root extract, Japanese angelica root water, *Calendula officinalis* flower extract, oil soluble *Calendula officinalis* flower extract, soy milk powder, peach seed extract, Bitter orange peel extract, *Houttuynia cordata* extract, *Solanum lycopersicum* (tomato) extract, *Potentilla tormentilla* Schrk (Rosaceae) extract, fermented soybeans extract, Ginseng extract, oil soluble Ginseng extract, *Allium sativum* (garlic) extract, wild rose extract, oil soluble wild rose extract, malt extract, malt root extract, *Ophiopogon* tuber extract, parsley extract, rye leaf juice concentrate, peppermint distillate, witch hazel distillate, witch hazel extract, rose extract, *parietaria* extract, *Isodonis japonicus* extract, *Eriobotrya japonica* leaf extract, oil soluble *Eriobotrya japonica* leaf extract, coltsfoot extract, hoelen extract, *Ruscus aculeatus* root extract, powdered *Ruscus aculeatus* root extract, grape extract, grape leaf extract, grape water, Hayflower extract, *Luffa cylindrica* fruit extract, *Luffa cylindrica* fruit water, *Carthamus tinctorius* (safflower) extract, oil soluble *Tilia platyphyllos* extract, linden distillate, *Paeonia suffruticosa* (peony) extract, *Humulus lupulus* (hops) extract, oil soluble *Humulus lupulus* (hops) extract, pine extract, *Silybum marianum* (milk thistle) extract, *Aesculus hippocastanum* (horse chestnut) extract, oil soluble *Aesculus hippocastanum* (horse chestnut) extract, *Sapindus mukurossi* extract, *Melissa officinalis* (balm mint) extract, *Melilotus officinalis* (melilot) extract, *Prunus persica* (peach)leaf extract, oil soluble *Prunus persica* (peach)leaf extract, bean sprouts extract, *Centaurea cyanus* flower extract, *Centaurea cyanus* flower distillate, *Eucalyptus globulus* extract, Saxifrage extract, *Lilium* (lily) extract, *Coix* seed extract, oil soluble *Coix* seed extract, *Artemisia princeps* pampanini extract, *Artemisia princeps* pampanini water, *Lavandula angustifolia* (lavender) extract, *Lavandula angustifolia* (lavender) water, apple extract, *Ganoderma lucidum* extract, *Lactuca sativa* (lettuce) extract, lemon extract, *Astragalus sinicus* extract, *Rosa centifolia* (rose) flower water, *Rosemarinus officinalis* (rosemary) extract, oil soluble *Rosemarinus officinalis* (rosemary) extract, *Anthemis nobilis* extract and *Sanguisorba officinalis* extract;

amino acids and peptides such as glycine, alanine, valine, leucine, isoleucine, serine, threonine, phenylalanine, tyrosine, tryptophan, cystine, cysteine, methionine, proline, hydroxyproline, aspartic acid, asparagine, glutamic acid, glutamine, arginine, histidine, lysine, γ-aminobutyric acid, DL-pyrrolidonecarboxylic acid, ε-aminocaproic acid, hydrolyzed elastin, water soluble elastin, hydrolyzed collagen, water soluble collagen, casein, glutathione, wheat peptides and soybean peptide;

vitamins and factors acting like a vitamin such as: vitamin A and analogues thereof such as retinol, retinal, retinoic acid, retinol acetate and retinol palmitate; carotenoids such as α-carotene, β-carotene, γ-carotene, δ-carotene, lycopene, zeaxanthin, cryptoxanthin, echinenon and astaxanthin; vitamin $B_1$ and analogues thereof such as thiamines; vitamin $B_2$ and analogues thereof such as riboflavin; vitamin $B_6$ and analogues thereof such as pyridoxine, pyridoxal and pyridoxamine; vitamin $B_{12}$ and analogues thereof such as cyanocobalamin; folic acids, nicotinic acid, nicotinamide, pantothenic acids, biotins; vitamin C and analogues thereof such as L-ascorbic acid, sodium L-ascorbate, L-ascorbyl stearate, L-ascorbyl palmitate, L-ascorbyl dipalmitate, L-ascorbyl tetraisopalmitate, L-ascorbate sulfate disodium ester, magnesium L-ascorbyl phosphate, sodium L-ascorbyl phosphate and L-ascorbate-2-glucoside; vitamin D and analogues thereof such as ergocalciferol and cholecalciferol; vitamin E and analogues thereof such as d-α-tocopherol, DL-α-tocopherol, dl-α-tocopherol acetate, dl-α-tocopherol succinate, β-tocopherol, γ-tocopherol and d-ε-tocopherol; ubiquinones, vitamin K and analogues thereof, carnitine, ferulic acid, γ-oryzanol, α-lipoic acid and orotic acid;

antiseptic agents such as benzoic acid, sodium benzoate, undecylenic acid, salicylic acid, sorbic acid, potassium sorbate, dehydroacetic acid, sodium dehydroacetate, isobutyl parahydroxybenzoate, isopropyl parahydroxybenzoate, ethyl parahydroxybenzoate, butyl parahydroxybenzoate, propyl parahydroxybenzoate, benzyl parahydroxybenzoate, methyl parahydroxybenzoate, sodium parahydroxybenzoate methyl, phenoxyethanol, light sensitive dye No. 101, light sensitive dye No. 201 and light sensitive dye No. 401;

antioxidizing agents such as butylhydroxyanisole, butylhydroxytoluene, propyl gallate, erythorbic acid, sodium erythorbate, para-hydroxyanisole and octyl gallate;

chelating agents to bind to a metal ion such as trisodium ethylenediamine hydroxyethyl triacetate, edetic acid, disodium edetate, trisodium edetate, tetrasodium edetate, sodium citrate, gluconic acid, phytic acid, sodium polyphosphate and sodium metaphosphate;

moisturizing agents such as hyaluronic acid, sodium hyaluronate, sodium chondroitin sulfate, sodium lactate, sodium pyrrolidone carboxylate, betaine, lactic acid bacteria fermented solution, yeast extract and ceramide;

anti-inflammatory agents such as glycyrrhizic acid, trisodium glycyrrhizinate, dipotassium glycyrrhizinate, monoammonium glycyrrhizinate, β-glycyrrhetinic acid, glycerin glycyrrhetinate, stearyl glycyrrhetinate, lysozyme chloride, hydrocortisone and allantoin;

pH adjusting agents such as sodium hydroxide, potassium hydroxide and triethanolamine;

salts such as sodium chloride, potassium chloride, magnesium chloride and sodium sulfate;

α-hydroxy acids such as citric acid, glycolic acid, tartaric acid and lactic acid;

whitening agents such as arbutin, α-arbutin and placenta extract;

essential oils such as *Archangelica officinalis* (angelica) oil, *Canangium odoratum* (ylang ylang) oil, *Canarium luzonicum* (elemi) oil, orange oil, *Chamomilla recutita* (matricaria) oil, *Anthemis nobilis* oil, *Elettaria cardamom* (cardamon) oil, *Acorus calamus* (calamus) oil, *Ferula galbaniflua* (galbanum) oil, *Cinnamomum camphora* (camphor) oil, *Daucus carota* (carrot) seed oil, *Salvia sclarea* (clary sage) oil, *Citrus paradisi* (grapefruit) oil, *Eugenia caryophyllus* (clove) oil, Cinnamon bark oil, *Coriandrum sativum* (coriander) oil, *Cupressus sempervirens* (cypress) oil, *Santalum album* (sandalwood) oil, *Juniperus virginiana* (cedarwood) oil, *Cympogon nardus* (citronella) oil, *Cinnamomum zeylanicum* (Cinnamon) leaf oil, *Jasmine officinale* (jasmine) absolute oil, *Juniperus communis* (juniper Berry) oil, *Zingiber officinale* (ginger) extract, *Mentha spicata* (spearmint) oil, *Salvia officinalis* (sage) oil, cedar oil, *Pelargonium grabeolens* (geranium) oil, *Thymus vulgaris* (thyme) oil, *Melaleuca alternifolia* (tea tree) oil, *Myristica fragrans* (nutmeg) oil, *Melaleuca qui.viridiflara* (niaouli) oil, *Citrus aurantium* (neroli) oil, pine oil, *Ocimum basilicum* (basil) oil, *Mentha arvensis* oil, *Pogostemon patchouli* (patchouli) oil, *Cymbopogon martini* (palmarosa) oil, *Foeniculum vulgare* (fennel) oil, *Citrus bigaradia* (petitgrain) oil, *Piper nigrum* (black pepper) oil, *Boswellia carterii* (frankincense) oil, *Vetiveria zizanoides* (vetivert) oil, *Mentha piperita* (peppermint) oil, *Citrus bergamia* (bergamot) oil, benzoin oil, *Aniba rosaeodora* (bois de rose) oil, *Origanum majorana* (marjoram) oil, mandarin oil, *Conumiphora myrrha* (myrrh) oil, *Melissa officinalis* (balm mint) oil, *Eucalyptus globulus* oil, *Citrus junos* oil, *Citrus aurantifolia* (lime) oil, *Ravensare aromaticum* (ravensare) oil, *Lavandula latifolia* (lavandin) oil, *Lavandula angustifolia* (lavender) oil, *Tilia vulgaris* (linden) oil, lemon oil, lemon grass oil, rose oil, *Aniba rosaeodora* (rosewood) oil, *Rosemarinus officinalis* (rosemary) oil and *Levisticum officinale* (lovage) oil;

terpenes such as limonene, pinene, terpinene, terpinolene, myrcene and longifeelene;

fragrance, water, and the like.

The above components can be contained in the agent for skin external use within limits not detrimental to the effects of the present invention, and they can be contained in amounts of usually 0.01 to 90% by mass, preferably 0.1 to 25% by mass, more preferably 0.3 to 10% by mass, in the whole amount of the agent for skin external use.

Agent for Skin External Use, Cosmetic

The agent for skin external use of the invention contains the salt of higher fatty acid ester of ascorbic acid-2-phosphoric acid ester and the polyhydric alcohol, and can further contain the aforesaid other components when needed. The most embodiments of the agent for skin external use of the invention are cosmetics. In the present description, the term "cosmetics" is used in a broad sense including skin milk, skin cream, foundation cream, massage cream, cleansing cream, shaving cream, cleansing foam, skin toner, lotion, pack, shampoo, rinse, hair glowing agent, hair tonic, hair dye, hair treatment agent, tooth paste, gargle, permanent waving agent, ointment, bath agent, body soap, etc., irrespective of the categories, provided that they are brought into contact with the skin when used. Further, the term "cosmetics" is used in a broad sense irrespective of age or sex of users.

When the agent for skin external use of the invention is a cosmetic, substances generally employable for cosmetics, which are selected from the aforesaid other components (C), can be employed, and in addition thereto, the existing cosmetic materials other than the components (C) can be further employed.

For example, there can be employed all the cosmetic materials described in "The Japanese Standards of Cosmetic Ingredients, 2nd Edition Annotation", edited by Society of Japanese Pharmacopoeia, 1984 (Yakuji Nippo, Ltd.), "The Japanese Cosmetic Ingredients Codex", supervised by the Ministry of Health and Welfare, Pharmaceutical Affairs Bureau, Evaluation and Licensing Division, 1993 (Yakuji Nippo, Ltd.), "Supplement to the Japanese Cosmetic Ingredients Codex", supervised by the Ministry of Health and Welfare, Pharmaceutical Affairs Bureau, Evaluation and Licensing Division, 1993 (Yakuji Nippo, Ltd.), "The Comprehensive Licensing Standards of Cosmetics by Category", supervised by the Ministry of Health and Welfare, Pharmaceutical Affairs Bureau, Evaluation and Licensing Division, 1993 (Yakuji Nippo, Ltd.), "The Japanese Cosmetic Compounding Ingredients by Category", supervised by the Ministry of Health and Welfare, Pharmaceutical Affairs Bureau, Evaluation and Licensing Division, 1997 (Yakuji Nippo, Ltd.), and "Cosmetic Material Dictionary", 1991 (Nikko Chemicals).

These cosmetic materials can be contained in such amounts that the total of these materials and the aforesaid other components (C) is in the range of 0.01 to 90% by mass, preferably 0.1 to 25% by mass, more preferably 0.3 to 10% by mass, in the whole amount of the cosmetic.

The agent for skin external use and the cosmetic of the invention can be prepared by dissolving, mixing or dispersing the above components in given amounts in accordance with a conventional process corresponding to its embodiment.

Method for Stabilizing Agent for Skin External Use Containing Salt of Higher Fatty Acid Ester of Ascorbic Acid-2-phosphoric Acid Ester, and Stabilizer In the agent for skin external use of the invention, a salt of higher fatty acid ester of ascorbic acid-2-phosphoric acid ester and a polyhydric alcohol are both contained, as described above, and therefore, occurrence of turbidity or precipitation with time can be inhibited even when the agent for skin external use is prepared using the salt of higher fatty acid ester of ascorbic acid-2-phosphoric acid ester.

In other words, by the use of a polyhydric alcohol as a stabilizer to allow the polyhydric alcohol and the salt of higher fatty acid ester of ascorbic acid-2-phosphoric acid ester to be present together in the agent for skin external use, the agent for skin external use containing the salt of higher fatty acid ester of ascorbic acid-2-phosphoric acid ester can be stabilized. Accordingly, the polyhydric alcohol can be favorably used as a stabilizer for the agent for skin external use containing a salt of higher fatty acid ester of ascorbic acid-2-phosphoric acid ester.

Effects of the Invention

According to the present invention, occurrence of turbidity or precipitation with time can be prevented to enhance stability even when the agent for skin external use is prepared using a specific salt of higher fatty acid ester of ascorbic acid-2-phosphoric acid ester. Accordingly, the present invention is useful for all agents for skin external use, particularly cosmetics.

EXAMPLES

The present invention is further described with reference to the following examples, but it should be construed that the invention is in no way limited to those examples.

As the glycerin described below, glycerin having a glycerin content of not less than 98% by mass was used. The unit of numerals in the tables is % by mass and total of the components in the tables is 100% by mass.

In the examples, evaluation of turbidity and precipitation was carried out based on the following criteria.
(1) Evaluation of Turbidity
Occurrence of turbidity was visually observed and evaluated based on the following criteria.
–: Occurrence of turbidity is not observed at all.
±: Occurrence of turbidity is slightly observed.
+: Occurrence of turbidity is conspicuous.
(2) Evaluation of Precipitation
Occurrence of precipitation was visually observed and evaluated based on the following criteria.
–: Occurrence of precipitation is not observed at all.
±: Occurrence of precipitation is slightly observed.
+: Occurrence of precipitation is conspicuous.

Examples 1-4 and Comparative Example 1

The components 1 to 6 shown in Table 1 were homogeneously blended in a blending ratio shown in Table 1, then stirred and dissolved to obtain a lotion. The resulting lotion was allowed to stand still at 40° C. for 1 month, the evaluation of occurrence of turbidity and precipitation with time was performed. The evaluation was performed by visual observation based on the above criteria. The results of the evaluation of occurrence of turbidity and precipitation performed after the lotion was allowed to stand still at 40° C. for 1 month are set forth in Table 1.

It can be seen from Table 1 that occurrence of turbidity and precipitation was more effectively inhibited and stability of the lotion was enhanced in Examples 1 to 4 as compared with those in Comparative Example 1.

TABLE 1

|   |   | Comp. Ex. 1 | Ex. 1 | Ex. 2 | Ex. 3 | Ex. 4 |
|---|---|---|---|---|---|---|
| 1 | Ascorbic acid-2-phosphoric acid-6-palmitic acid sodium salt | 2 | 2 | 2 | 2 | 2 |
| 2 | Citric acid | 0.08 | 0.08 | 0.08 | 0.08 | 0.08 |
| 3 | Ethanol | 5 | 5 | 5 | 5 | 5 |
| 4 | Propylene glycol | – | 5 | 10 | 12 | 15 |
| 5 | Methyl para-hydroxybenzoate | 0.2 | 0.2 | 0.2 | 0.2 | 0.2 |
| 6 | Purified water | Rest | Rest | Rest | Rest | Rest |
|   | Turbidity | + | ± | ± | – | – |
|   | Precipitation | – | – | – | – | – |

In Example 1 and Comparative Example 1, the propylene glycol concentration was determined as follows by gas chromatography.

A sample of 1 g was diluted with acetone to give a 10 ml of a sample solution. Then, a calibration curve of a standard solution of propylene glycol was made from a gas chromatogram, and from the calibration curve, the amount of propylene glycol in the sample solution was determined. The conditions of gas chromatography are as follows.
Apparatus: HP6890
Column: J&W Scientific DB-1 (inner diameter: 0.32 mm, length: 30 m, film thickness: 5 μm)
Column oven temperature: 50° C. (1 minute), heating at 20° C./minute, 320° C. (10 minutes)
Carrier gas: He
Column flow rate: 1.5 ml/minute
Injection mode: split (1:50)
Injection quantity: 1 μl
FID temperature: 320° C.

As a result, the propylene glycol concentrations in Example 1 and Comparative Example 1 were 5% by mass and 0% by mass, respectively.

Examples 5-9 and Comparative Example 2

The components 1 to 5 shown in Table 2 were homogeneously blended in a blending ratio shown in Table 2, then stirred and dissolved to obtain a lotion. The resulting lotion was allowed to stand still at 40° C. for 1 month, the evaluation of occurrence of turbidity and precipitation with time was performed. The evaluation was performed by visual observation based on the above criteria. The results of the evaluation of occurrence of turbidity and precipitation performed after the lotion was allowed to stand still at 40° C. for 1 month are set forth in Table 2.

It can be seen from Table 2 that occurrence of turbidity and precipitation was more effectively inhibited and stability of the lotion was enhanced in Examples 5 to 9 as compared with those in Comparative Example 2.

TABLE 2

|   |   | Comp. Ex. 2 | Ex. 5 | Ex. 6 | Ex. 7 | Ex. 8 | Ex. 9 |
|---|---|---|---|---|---|---|---|
| 1 | Ascorbic acid-2-phosphoric acid-6-palmitic acid sodium salt | 0.7 | 2 | 2 | 2 | 2 | 2 |
| 2 | Citric acid | 0.03 | 0.08 | 0.08 | 0.08 | 0.08 | 0.08 |
| 3 | Glycerin | – | 5 | 10 | 15 | 90 | 95 |
| 4 | Methyl para-hydroxybenzoate | 0.1 | 0.1 | 0.1 | 0.1 | 0.1 | 0.1 |
| 5 | Purified water | Rest | Rest | Rest | Rest | Rest | Rest |
|   | Turbidity | + | ± | ± | – | – | ± |
|   | Precipitation | – | – | – | – | – | – |

Examples 10-12 and Comparative Example 3

The components 1 to 10 shown in Table 3 were homogeneously blended in a blending ratio shown in Table 3, then stirred and dissolved to obtain a lotion. The resulting lotion was allowed to stand still at 40° C. for 1 month, the evaluation of occurrence of turbidity and precipitation with time was performed. The evaluation was performed by visual observation based on the above criteria. The results of the evaluation of occurrence of turbidity and precipitation performed after the lotion was allowed to stand still at 40° C. for 1 month are set forth in Table 3.

It can be seen from Table 3 that occurrence of turbidity and precipitation was more effectively inhibited and stability of the lotion was enhanced in Examples 10 to 12 as compared with those in Comparative Example 3.

TABLE 3

| | | Comp. Ex. 3 | Ex. 10 | Ex. 11 | Ex. 12 |
|---|---|---|---|---|---|
| 1 | Ascorbic acid-2-phosphoric acid-6-palmitic acid sodium salt | 1 | 1 | 1 | 1 |
| 2 | Ethanol | 4 | 4 | 4 | 4 |
| 3 | Propylene glycol | – | 15 | – | – |
| 4 | 1,3-Butanediol | – | – | 15 | – |
| 5 | Dipropylene glycol | – | – | – | 15 |
| 6 | Trehalose | – | 0.05 | 0.05 | 0.05 |
| 7 | Citric acid | 0.2 | 0.2 | 0.2 | 0.2 |
| 8 | Sodium citrate | 0.2 | 0.2 | 0.2 | 0.2 |
| 9 | Methyl para-hydroxybenzoate | 0.1 | 0.1 | 0.1 | 0.1 |
| 10 | Purified water | Rest | Rest | Rest | Rest |
| | Turbidity | + | – | – | – |
| | Precipitation | – | – | – | – |

Examples 13-15 and Comparative Example 4

The components 1 to 10 shown in Table 4 were homogeneously blended in a blending ratio shown in Table 4, then stirred and dissolved to obtain a lotion. The resulting lotion was allowed to stand still at 40° C. for 1 month, the evaluation of occurrence of turbidity and precipitation with time was performed. The evaluation was performed by visual observation based on the above criteria. The results of the evaluation of occurrence of turbidity and precipitation performed after the lotion was allowed to stand still at 40° C. for 1 month are set forth in Table 4.

It can be seen from Table 4 that occurrence of turbidity and precipitation was more effectively inhibited and stability of the lotion was enhanced in Examples 13 to 15 as compared with those in Comparative Example 4.

TABLE 4

| | | Comp. Ex. 4 | Ex. 13 | Ex. 14 | Ex. 15 |
|---|---|---|---|---|---|
| 1 | Ascorbic acid-2-phosphoric acid-6-(2-hexyldecanoic acid) sodium salt | 1 | 1 | 1 | 1 |
| 2 | Ethanol | 4 | 4 | 4 | 4 |
| 3 | Propylene glycol | – | 15 | – | – |
| 4 | 1,3-Butanediol | – | – | 15 | – |
| 5 | Dipropylene glycol | – | – | – | 15 |
| 6 | Trehalose | – | 0.05 | 0.05 | 0.05 |
| 7 | Citric acid | 0.2 | 0.2 | 0.2 | 0.2 |
| 8 | Sodium citrate | 0.2 | 0.2 | 0.2 | 0.2 |
| 9 | Methyl para-hydroxybenzoate | 0.1 | 0.1 | 0.1 | 0.1 |
| 10 | Purified water | Rest | Rest | Rest | Rest |
| | Turbidity | + | – | – | – |
| | Precipitation | – | – | – | – |

Examples 16-21 and Comparative Example 5

The components 1 to 10 shown in Table 5 were homogeneously blended in a blending ratio shown in Table 5, then stirred and dissolved to obtain an essence. The resulting essence was allowed to stand still at 40° C. for 1 month, the evaluation of occurrence of turbidity and precipitation with time was performed. The evaluation was performed by visual observation based on the above criteria. The results of the evaluation of occurrence of turbidity and precipitation performed after the essence was allowed to stand still at 40° C. for 1 month are set forth in Table 5.

It can be seen from Table 5 that occurrence of turbidity and precipitation was more effectively inhibited and stability of the essence was enhanced in Examples 16 to 21 as compared with those in Comparative Example 5.

TABLE 5

| | | Comp. Ex. 5 | Ex. 16 | Ex. 17 | Ex. 18 | Ex. 19 | Ex. 20 | Ex. 21 |
|---|---|---|---|---|---|---|---|---|
| 1 | Ascorbic acid-2-phosphoric acid-6-stearic acid sodium salt | 3 | 3 | 3 | 3 | 3 | 3 | 3 |
| 2 | 1,3-Butanediol | – | 5 | 6 | 7.5 | 15 | 10 | 10 |
| 3 | Glycerin | – | 3 | 3.6 | 4.5 | 9 | 8 | 16 |
| 4 | Propylene glycol | – | 2 | 2.4 | 3 | 6 | 1 | 4 |
| 5 | Sodium hyaluronate | 0.2 | 0.2 | 0.2 | 0.2 | 0.2 | 0.2 | 0.2 |
| 6 | Ethanol | 3 | 3 | 3 | 3 | 3 | 3 | 3 |
| 7 | Hydroxyethyl cellulose | 0.1 | 0.1 | 0.1 | 0.1 | 0.1 | 0.1 | 0.1 |
| 8 | Polyethylene glycol (60) hydrogenated castor oil | 0.1 | 0.1 | 0.1 | 0.1 | 0.1 | 0.1 | 0.1 |
| 9 | Methyl Para-hydroxybenzoate | 0.1 | 0.1 | 0.1 | 0.1 | 0.1 | 0.1 | 0.1 |
| 10 | Purified water | Rest | Rest | Rest | Rest | Rest | Rest | Rest |

TABLE 5-continued

|  | Comp. Ex. 5 | Ex. 16 | Ex. 17 | Ex. 18 | Ex. 19 | Ex. 20 | Ex. 21 |
|---|---|---|---|---|---|---|---|
| Turbidity | + | ± | − | − | − | − | − |
| Precipitation | ± | ± | − | − | − | − | − |

Examples 22-27 and Comparative Example 6

The components 1 to 10 shown in Table 6 were homogeneously blended in a blending ratio shown in Table 6, then stirred and dissolved to obtain an essence. The resulting essence was allowed to stand still at 40° C. for 1 month, the evaluation of occurrence of turbidity and precipitation with time was performed. The evaluation was performed by visual observation based on the above criteria. The results of the evaluation of occurrence of turbidity and precipitation performed after the essence was allowed to stand still at 40° C. for 1 month are set forth in Table 6.

It can be seen from Table 6 that occurrence of turbidity and precipitation was more effectively inhibited and stability of the essence was enhanced in Examples 22 to 27 as compared with those in Comparative Example 6.

Examples 28-33 and Comparative Example 7

The components 1 to 8 shown in Table 7 were homogeneously blended in a blending ratio shown in Table 7, then stirred and dissolved to obtain a lotion. The resulting lotion was allowed to stand still at 40° C. for 1 month, the evaluation of occurrence to turbidity and precipitation with time was performed. The evaluation was performed by visual observation based on the above criteria. The results of the evaluation of occurrence of turbidity and precipitation performed after the lotion was allowed to stand still at 40° C. for 1 month are set forth in Table 7.

TABLE 6

|  |  | Comp. Ex. 6 | Ex. 22 | Ex. 23 | Ex. 24 | Ex. 25 | Ex. 26 | Ex. 27 |
|---|---|---|---|---|---|---|---|---|
| 1 | Ascorbic acid-2-phosphoric acid-6-isostearic acid sodium salt | 3 | 3 | 3 | 3 | 3 | 3 | 3 |
| 2 | 1,3-Butanediol | − | 5 | 6 | 7.5 | 15 | 10 | 10 |
| 3 | Glycerin | − | 3 | 3.6 | 4.5 | 9 | 8 | 16 |
| 4 | Propylene glycol | − | 2 | 2.4 | 3 | 6 | 1 | 4 |
| 5 | Sodium hyaluronate | 0.2 | 0.2 | 0.2 | 0.2 | 0.2 | 0.2 | 0.2 |
| 6 | Ethanol | 3 | 3 | 3 | 3 | 3 | 3 | 3 |
| 7 | Hydroxyethyl cellulose | 0.1 | 0.1 | 0.1 | 0.1 | 0.1 | 0.1 | 0.1 |
| 8 | Polyethylene glycol (60) hydrogenated castor oil | 0.1 | 0.1 | 0.1 | 0.1 | 0.1 | 0.1 | 0.1 |
| 9 | Methyl para-hydroxybenzoate | 0.1 | 0.1 | 0.1 | 0.1 | 0.1 | 0.1 | 0.1 |
| 10 | Purified water | Rest | Rest | Rest | Rest | Rest | Rest | Rest |
|  | Turbidity | + | ± | − | − | − | − | − |
|  | Precipitation | ± | ± | − | − | − | − | − |

It can be seen from Table 7 that occurrence of turbidity and precipitation was more effectively inhibited and stability of the lotion was enhanced in Examples 28 to 33 as compared with those in Comparative Example 7.

TABLE 7

|  |  | Comp. Ex. 7 | Ex. 28 | Ex. 29 | Ex. 30 | Ex. 31 | Ex. 32 | Ex. 33 |
|---|---|---|---|---|---|---|---|---|
| 1 | Ascorbic acid-2-phosphoric acid-6-palmitic acid sodium salt | 1 | 1 | 1 | 1 | 1 | 1 | 1 |
| 2 | 1,2-Pentanediol | − | 0.1 | 1 | 5 | − | − | − |
| 3 | 1,2-Hexanediol | − | − | − | − | 0.1 | 1 | 5 |
| 4 | Trehalose | − | 0.05 | 0.05 | 0.05 | 0.05 | 0.05 | 0.05 |
| 5 | Citric acid | 0.2 | 0.2 | 0.2 | 0.2 | 0.2 | 0.2 | 0.2 |
| 6 | Sodium citrate | 0.2 | 0.2 | 0.2 | 0.2 | 0.2 | 0.2 | 0.2 |
| 7 | Methyl Para-hydroxybenzoate | 0.1 | 0.1 | 0.1 | 0.1 | 0.1 | 0.1 | 0.1 |
| 8 | Purified water | Rest | Rest | Rest | Rest | Rest | Rest | Rest |
|  | Turbidity | + | − | − | − | − | − | − |
|  | Precipitation | − | − | − | − | − | − | − |

Examples 34-39 and Comparative Example 8

The components 1 to 8 shown in Table 8 were homogeneously blended in a blending ratio shown in Table 8, then stirred and dissolved to obtain a lotion. The resulting lotion was allowed to stand still at 40° C. for 1 month, the evaluation of occurrence of turbidity and precipitation with time was performed. The evaluation was performed by visual observation based on the above criteria. The results of the evaluation of occurrence of turbidity and precipitation performed after the lotion was allowed to stand still at 40° C. for 1 month are set forth in Table 8.

It can be seen from Table 8 that occurrence of turbidity and precipitation was more effectively inhibited and stability of the lotion was enhanced in Examples 34 to 39 as compared with those in Comparative Example 8.

TABLE 8

| | | Comp. Ex. 8 | Ex. 34 | Ex. 35 | Ex. 36 | Ex. 37 | Ex. 38 | Ex. 39 |
|---|---|---|---|---|---|---|---|---|
| 1 | Ascorbic acid-2-phosphoric acid-6-(2-hexyldecanoic acid) sodium salt | 1 | 1 | 1 | 1 | 1 | 1 | 1 |
| 2 | 1,2-Pentanediol | – | 0.1 | 1 | 5 | – | – | – |
| 3 | 1,2-Hexanediol | – | – | – | – | 0.1 | 1 | 5 |
| 4 | Trehalose | – | 0.05 | 0.05 | 0.05 | 0.05 | 0.05 | 0.05 |
| 5 | Citric acid | 0.2 | 0.2 | 0.2 | 0.2 | 0.2 | 0.2 | 0.2 |
| 6 | Sodium citrate | 0.2 | 0.2 | 0.2 | 0.2 | 0.2 | 0.2 | 0.2 |
| 7 | Methyl para-hydroxybenzoate | 0.1 | 0.1 | 0.1 | 0.1 | 0.1 | 0.1 | 0.1 |
| 8 | Purified water | Rest | Rest | Rest | Rest | Rest | Rest | Rest |
| | Turbidity | + | – | – | – | – | – | – |
| | Precipitation | – | – | – | – | – | – | – |

Examples 40-41 and Comparative Example 9

The components 1 to 9 shown in Table 9 were homogeneously blended in a blending ratio shown in Table 9, then stirred and dissolved to obtain an essence. The resulting essence was allowed to stand still at 40° C. for 1 month, the evaluation of occurrence of turbidity and precipitation with time was performed. The evaluation was performed by visual observation based on the above criteria. The results of the evaluation of occurrence of turbidity and precipitation performed after the essence was allowed to stand still at 40° C. for 1 month are set forth in Table 9.

It can be seen from Table 9 that occurrence of turbidity and precipitation was more effectively inhibited and stability of the essence was enhanced in Examples 40 to 41 as compared with those in Comparative Example 9.

TABLE 9

| | | Comp. Ex. 9 | Ex. 40 | Ex. 41 |
|---|---|---|---|---|
| 1 | Ascorbic acid-2-phosphoric acid-6-palmitic acid | 1 | 2 | 2 |
| 2 | 1,2-Pentanediol | – | 8 | – |
| 3 | 1,2-Hexanediol | – | – | 8 |
| 4 | Sodium hyaluronate | 0.2 | 0.2 | 0.2 |
| 5 | Polyethylene glycol (60) hydrogenated castor oil | 0.1 | 0.1 | 0.1 |
| 6 | Hydroxyethyl cellulose | 0.1 | 0.1 | 0.1 |
| 7 | Methyl para-hydroxybenzoate | 0.1 | 0.1 | 0.1 |
| 8 | Phenoxyethanol | 0.02 | 0.02 | 0.02 |
| 9 | Purified water | Rest | Rest | Rest |
| | Turbidity | + | – | – |
| | Precipitation | ± | – | – |

Examples 42-43 and Comparative Example 10

The components 1 to 9 shown in Table 10 were homogeneously blended in a blending ratio shown in Table 10, then stirred and dissolved to obtain an essence. The resulting essence was allowed to stand still at 40° C. for 1 month, the evaluation of occurrence of turbidity and precipitation with time was performed. The evaluation was performed by visual observation based on the above criteria. The results of the evaluation of occurrence of turbidity and precipitation performed after the essence was allowed to stand still at 40° C. for 1 month are set forth in Table 10.

It can be seen from Table 10 that occurrence of turbidity and precipitation was more effectively inhibited and stability of the essence was enhanced in Examples 42 to 43 as compared with those in Comparative Example 10.

TABLE 10

| | | Comp. Ex. 10 | Ex. 42 | Ex. 43 |
|---|---|---|---|---|
| 1 | Ascorbic acid-2-phosphoric acid-6-(2-hexyldecanoic acid) sodium salt | 1 | 2 | 2 |
| 2 | 1,2-Pentanediol | – | 8 | – |
| 3 | 1,2-Hexanediol | – | – | 8 |
| 4 | Sodium hyaluronate | 0.2 | 0.2 | 0.2 |
| 5 | Polyethylene glycol (60) hydrogenated castor oil | 0.1 | 0.1 | 0.1 |
| 6 | Hydroxyethyl cellulose | 0.1 | 0.1 | 0.1 |
| 7 | Methyl para-hydroxybenzoate | 0.1 | 0.1 | 0.1 |
| 8 | Phenoxyethanol | 0.02 | 0.02 | 0.02 |
| 9 | Purified water | Rest | Rest | Rest |
| | Turbidity | + | – | – |
| | Precipitation | ± | – | – |

INDUSTRIAL APPLICABILITY

According to the present invention, occurrence of turbidity or precipitation with time can be prevented to enhance stability even when the agent for skin external use is prepared using a specific salt of higher fatty acid ester of ascorbic acid-2-phosphoric acid ester. Therefore, the present invention is useful for all agents for skin external use, particularly cosmetics.

The invention claimed is:

1. An agent for skin external use, comprising:
   a salt of higher fatty acid ester of ascorbic acid-2-phosphoric acid ester in an amount of 0.01 to 20% by mass, said higher fatty acid ester of ascorbic acid-2-phosphoric acid ester of the following formula (1):

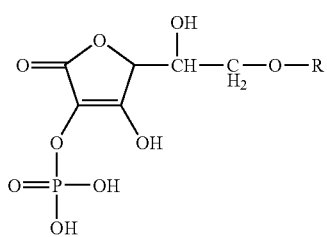

Formula (1)

wherein R is a residual group of an aliphatic carboxylic acid having 10 to 20 carbon atoms, and 1,2-pentanediol or 1,2-hexanediol in an amount of 0.05 to 12% by mass.

2. The agent for skin external use as claimed in claim 1, wherein R in the formula (1) is a residual group of lauric acid, myristic acid, palmitic acid, stearic acid, 2-hexyldecanoic acid or isostearic acid.

3. The agent for skin external use as claimed in claim 1, wherein R in the formula (1) is a residual group of palmitic acid.

4. The agent for skin external use as claimed in claim 1, wherein R in the formula (1) is a residual group of 2-hexyldecanoic acid.

5. The agent for skin external use as claimed in claim 1, wherein the salt of higher fatty acid ester of ascorbic acid-2-phosphoric acid ester is a Na salt, a K salt, a Mg salt or a Zn salt.

6. The agent for skin external use as claimed in claim 1, wherein water is further contained.

7. A cosmetic comprising the agent for skin external use of claim 1.

8. A method for stabilizing an agent for skin external use containing a salt of higher fatty acid ester of ascorbic acid-2-phosphoric acid ester, said higher fatty acid ester of ascorbic acid-2-phosphoric acid ester of the following formula (1):

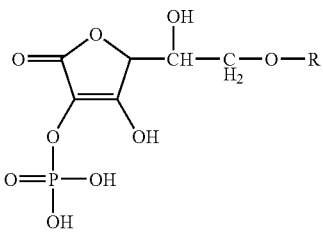

Formula (1)

wherein R is a group of an aliphatic carboxylic acid having 10 to 20 carbon atoms, comprising adding 1,2-pentanediol or 1,2-hexanediol or both to said salt.

9. An agent for skin external use, comprising:
   a salt of higher fatty acid ester of ascorbic acid-2-phosphoric acid ester, said higher fatty acid ester of ascorbic acid-2-phosphoric acid ester of the following formula (1):

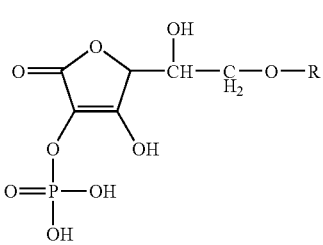

Formula (1)

wherein R is a residual group of an aliphatic carboxylic acid having 10 to 20 carbon atoms, and 1,2-hexanediol contained in an amount of not less than 0.05% by mass and less than 12% by mass.

10. The agent for skin external use as claimed in claim 9, wherein R is a residual group of an aliphatic carboxylic acid selected from the group consisting of palmitic acid, 2-hexyldecanoic acid, stearic acid and isostearic acid.

* * * * *